United States Patent [19]
Hui et al.

[11] Patent Number: 5,650,305
[45] Date of Patent: Jul. 22, 1997

[54] METHOD TO PRODUCE HYBRID CELLS BY ELECTROFUSION

[75] Inventors: Sek Wen Hui, Williamsville; Li Lin-Hong, Buffalo; Mary L. Hensen, East Aurora; Ya Li Zhao, Buffalo, all of N.Y.

[73] Assignee: Health Research Inc., Buffalo, N.Y.

[21] Appl. No.: 649,771

[22] Filed: May 15, 1996

[51] Int. Cl.$^6$ ........................................... C12N 5/12
[52] U.S. Cl. .......................... 435/172.2; 435/173.6; 435/285.2
[58] Field of Search .................. 435/172.2, 173.6, 435/285.2, 172.3

[56] References Cited

U.S. PATENT DOCUMENTS 5,007,995  4/1991  Takahashi et al. ..................... 204/299

Primary Examiner—James Ketter
Attorney, Agent, or Firm—Hodgson, Russ, Andrews, Woods & Goodyear

[57] ABSTRACT

A method and apparatus for electrofusing a cell pellet comprising a plurality of tiers of cells of two different cell types to be fused which results in the formation of hybrid cells with high efficiency and high viability. The method comprises subjecting the cell pellet, and a pulse medium in contact with the cell pellet, with multiple pulses of voltage. A method and apparatus for electrofusing a cell-vesicle pellet comprising a plurality of tiers of a cell type and of membrane vesicles, and wherein the membrane vesicles are loaded with an exogenous macromolecule to be delivered to the cell type during fusion, which results in the formation of fused cells containing the exogenous macromolecule with high efficiency and high viability. Alteratively, the membrane vesicles may contain at least one type of exogenous macromolecule inserted into its membrane. Fusion with a target cell results in the exogenous macromolecule being incorporated into the cell membrane of the target cell with high efficiency and high viability. The method comprises subjecting the cell-vesicle pellet, and a pulse medium in contact with the cell-vesicle pellet, with multiple pulses of voltage.

44 Claims, 5 Drawing Sheets

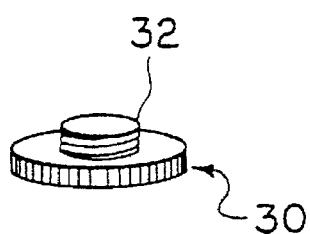
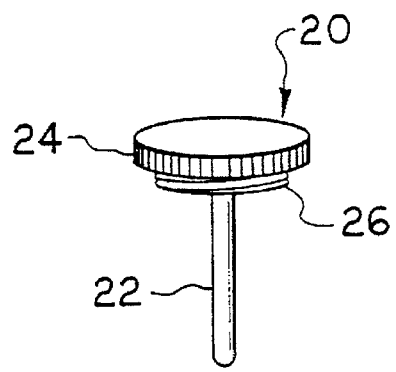
FIG. 5　　　　　FIG. 6
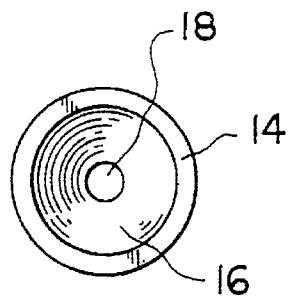
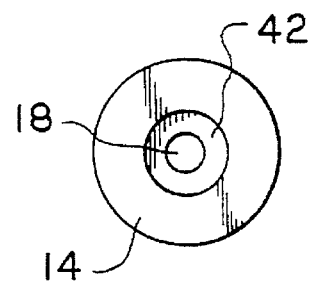
FIG. 7　　　　　FIG. 8
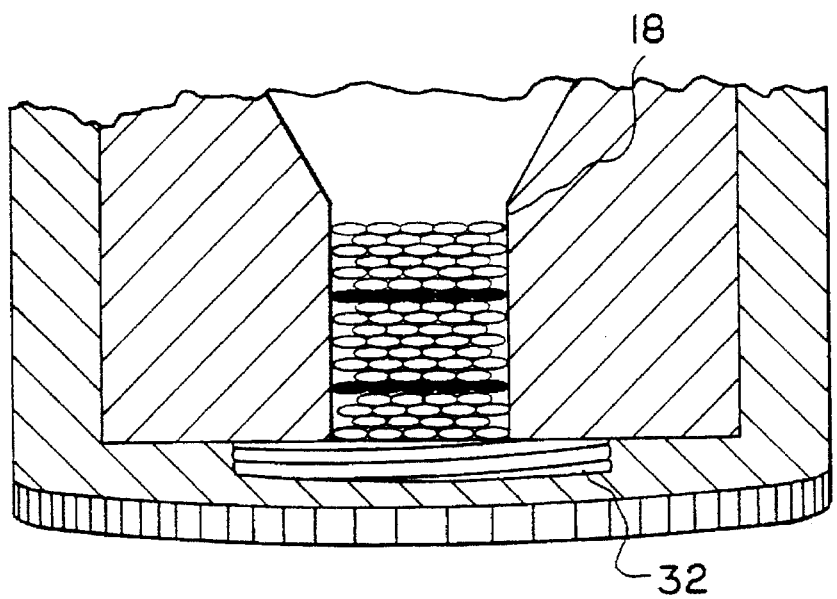
FIG. 9

METHOD TO PRODUCE HYBRID CELLS BY ELECTROFUSION

This invention was made with government support under grant GM30969 awarded by the National Institute of Health. The government has certain rights in the invention.

FIELD OF THE INVENTION

The present invention relates to a method and apparatus for facilitating high efficiency electrofusion between cells. More particularly, the invention relates to high efficiency fusion between cells of different sizes, or between cells and membrane vesicles, by applying electric pulses to a pellet comprising the target cells or cells and membrane vesicles to be fused.

BACKGROUND OF THE INVENTION

A number of techniques are known to those skilled in the art for inducing fusion between cells. These techniques include chemical fusion employing polyethylene glycol, use of biological fusogens such as viruses or viral proteins, and electrofusion of cells in suspension. Fusion by chemical means or via biological fusogens has certain limitations including the presence of chemical or biological contaminants inherent to the technique, resistance to fusion exhibited by some cell types, low efficiency, and cytotoxicity.

There are several advantages in producing cell hybrids by electrofusion. For example, fusion parameters can be easily and accurately electronically controlled to conditions depending on the cells to be fused. Further, electrofusion of cells has shown to the ability to increase fusion efficiency over that of fusion by chemical means or via biological fusogens. Electrofusion is performed by applying electric pulses to cells in suspension. By exposing cells to an alternating electric field, cells are brought close to each other in forming pearl chains in a process termed "dielectrophoresis alignment". Subsequent higher voltage pulses cause cells to come into closer contact, reversible electropores are formed in reversibly permeabilizing and mechanically breaking down cell membranes, resulting in fusion.

However, electrofusion of cells in suspension has certain limitations. The field strength of the electric pulse required to induce reversible electropores in permeabilizing membranes is cell size dependent. Thus, it is difficult to efficiently electrofuse cells of different sizes simultaneously. In such instances, larger cells are typically damaged by a given field strength required to induce reversible electropores in permeabilizing membranes of smaller cells. Further, it is known generally that the lower the medium conductivity, the more effective is the dielectrophoresis alignment for cells in suspension. A medium of higher conductivity may reduce the threshold field strength to induce mechanical breakdown of membranes. Thus, medium typically used for electrofusion of cells in suspension has a conductivity which is not optimal for both dielectrophoresis alignment and inducement of mechanical breakdown of membranes.

It would be desirable to provide a method and apparatus to fuse cells of heterogenous sizes, or to transfer macromolecules into target cells, with high efficiency and in the presence of a variety of pulse medium.

SUMMARY OF THE INVENTION

Accordingly, it is a primary object of the present invention to provide a simple and highly efficient method for electrofusing cells of different sizes.

It is another object of the present invention to provide a simple and highly efficient method for electrofusing cells of different sizes with high viability of resultant hybrid cells.

It is another object of the present invention to provide a simple and highly efficient method for electrofusing target cells and membrane vesicles in delivering exogenous macromolecules into the target cells.

It is another object of the present invention to provide a simple and highly efficient method for electrofusing target cells and membrane vesicles for inserting macromolecules (exogenous and/or endogenous) into the membranes of the target cells.

It is another object of the present invention to provide a simple and highly efficient method for electrofusing target cells and membrane vesicles in delivering exogenous macromolecules into the target cells while maintaining high viability.

It is another object of the present invention to provide a simple and highly efficient method for electrofusing target cells and membrane vesicles for inserting macromolecules (exogenous and/or endogenous) into the membranes of the target cells while maintaining high viability.

It is a further object of the present invention to provide an apparatus for performing highly efficient electrofusion of cells of different sizes.

It is a further object of the present invention to provide an apparatus for performing highly efficient electrofusion of target cells and membrane vesicles in delivering exogenous macromolecules into the target cells.

It is a further object of the present invention to provide an apparatus for performing highly efficient electrofusion of target cells and membrane vesicles for inserting exogenous macromolecules into the membranes of the target cells.

These and further features and advantages of the invention will be better understood from the description of the preferred embodiments when considered in relation to the figures in which:

SUMMARY OF THE FIGURES

FIG. 5 is a perspective view of a first embodiment of a bottom cap with bottom electrode for the apparatus for electrofusion.

FIG. 6 is a perspective view of a second embodiment of a cap with top electrode for the apparatus for electrofusion.

FIG. 7 is a top plan view of the open apparatus (without the top cap) for electrofusion.

FIG. 8 is a bottom plan view of the open apparatus (without the bottom) for electrofusion.

FIG. 9 is a sectional view of the pellet chamber of the apparatus for electrofusion, showing a pellet formed from a plurality of tiers of cells of two different cell types.

DESCRIPTION OF THE PREFERRED EMBODIMENTS

Definitions

Figure 1:
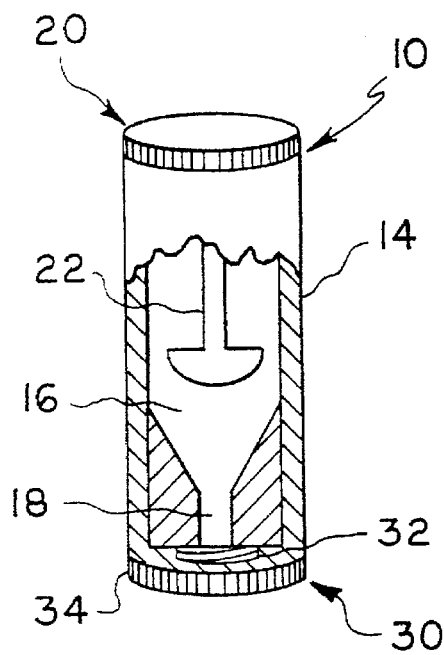
FIG. 1 is a partial sectional view of a first embodiment of an apparatus for electrofusion according to the method of the present invention.

The term "exogenous macromolecules" is used herein, for purposes of the specification and claims, to mean biomolecules including, but not limited to, peptides, proteins, antigens, antibodies, cell receptors, enzymes, polysaccharides, oligonucleotides, DNA, RNA, recombinant vectors, drugs, and dyes.

The term "endogenous macromolecules" is used herein, for purposes of the specification and claims, to mean biomolecules including, but not limited to, peptides, proteins, antigens, antibodies, cell receptors, enzymes, polysaccharides, naturally occuring in a membrane vesicle.

The term "cells" is used herein, for purposes of the specification and claims, to mean animal cells and particularly mammalian cells.

The term "membrane vesicles" is used herein, for purposes of the specification and claims, to mean erythrocyte ghosts, liposomes, vesicles of cell membranes, vesicles of reconstituted membranes, and other membraned carrier vehicles.

The term "cell pellet" is used herein, for purposes of the specification and claims, and as known in the art to mean a bolus of compacted cells formed by centrifugation of a cell suspension.

The term "cell-vesicle pellet" is used herein, for purposes of the specification and claims to mean a bolus of compacted cells and vesicles formed by centrifugation of a suspension or suspensions of cells and membrane vesicles.

The term "pellet" is used herein, for purposes of the specification and claims to either a cell pellet or a cell-vesicle pellet.

The term "high efficiency" is used herein, for purposes of the specification and claims to mean fusion efficiency greater than 40% and as high as 80–90% or greater as measured by content mixing and/or membrane dye mixing as described in more detail in the illustrative Examples.

The term "high viability" is used herein, for purposes of the specification and claims to mean viability greater than 50% and as high as 80–90% or greater as measured by, for example, dye exclusion as described in more detail in the illustrative Examples.

The term "pulse medium" is used herein, for purposes of the specification and claims to mean high conductivity or low conductivity buffered solutions which are used as medium in an electrofusion or an electroporation process. Such media are known in the art and include physiological buffers (e.g., PBS), and cell culture growth media (e.g., F10 medium with 15% serum supplement), as described in more detail in the illustrative Examples.

The term "tier" is used herein, for purposes of the specification and claims, to mean any one of a plurality (greater than 2) of layers. In one embodiment of the method according to the present invention, a pellet is formed of cells of alternating tiers, with each tier of cells arranged one above the other. In this embodiment, each tier comprises one type of cell occupying a certain thickness. Thus, in an example of a pellet of cells of different sizes to be fused, a first tier of cells comprises a first cell type; and a second tier of cells comprises a second cell type. If the pellet comprises additional tiers, such additional tiers alternate in cell composition between the first cell type and the second cell type. In another embodiment of the method according to the present invention, a pellet can mean a plurality of tiers of cells and membrane vesicles with each tier arranged one above the other. In this particular embodiment, each tier comprises either one type of cell, or comprises membrane vesicles, occupying a certain thickness. Thus, in an example of a pellet of cells and membrane vesicles to be fused, a first tier may comprise cells; and a second tier may comprise membrane vesicles. Desirably, the pellet comprises additional tiers (a total greater than 2), such tiers alternate in composition between the cells and the membrane vesicles in forming a plurality of tiers.

Unlike prior art methods of electrofusing cells in suspension, the method according to the present invention involves electrofusion of a cell pellet, or of a cell-vesicle pellet. Pelleting is utilized to artificially bring desired components (i.e., cells of different types, or cells and membrane vesicles) into close contact by centrifugation. The pellet comprises a plurality of tiers which may be formed using the apparatus according to the present invention, or other suitable means in the art. To the pellet is applied a plurality of pulses which induce mechanical breakdown of the membranes of the components, and subsequent colloidal osmotic swelling of the components to be fused, ultimately inducing electrofusion between the components. Unexpectedly, utilizing the method according to the present invention, electrofusion of components may be accomplished with high efficiency while maintaining high viability.

Electrofusion of pellets is considerably different than electrofusion of cells in suspension. First, a pellet comprising a plurality of tiers has a resistance which is usually much higher than the resistance of a chamber filled with either PBS, or a cell suspension, or cells in suspension in dielectrophoresis alignment. Due to this pellet resistance, a voltage applied to the electrofusion chamber containing the pellet will drop across the pellet. Thus, during breakdown of membranes induced by the voltage, cells in suspension experience the same electric field, whereas the voltage is concentrated across cells in pellets. Further, with the same applied voltages, the transmembrane potentials in pellets are much higher compared with that in cell suspensions. Thus, lower voltages may be applied to the pellet to achieve electrofusion as compared with that used in electrofusion in a cell suspension.

EXAMPLE 1

Apparatus for Electrofusion of a Pellet

In this example, embodiments of an apparatus to electrofuse a pellet comprising a plurality of tiers using the method of the present invention is described. Referring now to the drawings, FIGS. 1 to 5 show one embodiment of the electrofusion apparatus 10 of the present invention. Apparatus 10 preferably comprises a thick-walled cylinder 14. The thickness of the walls of the cylinder 14 provide it sufficient strength to be subjected to centrifugation without collapsing. Cylinder 14 is made of suitable material having low or no conductivity. Preferably cylinder 14 is made of a plastic material that has been injection molded to shape, or any other suitable fabricated material. For purposes of illustration only, and not limitation, the height of cylinder 14 may range from about 30 to about 40 millimeters (mm). For purposes of illustration only, and not limitation, the diameter of cylinder 14 may range from about 10 to about 15 mm. One factor to limit the range of dimensions of the height and diameter of cylinder 14 or apparatus 10 is the size of a centrifuge tube or holder into which it may be placed.

Figure 2:
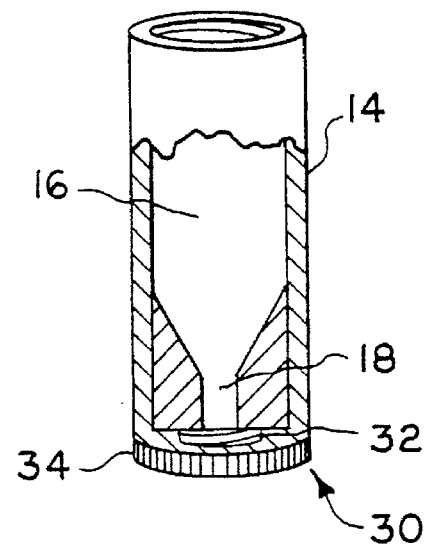
FIG. 2 is a partial sectional view of a first embodiment of an apparatus for electrofusion according to the method of the present invention.

As shown in FIGS. 1 & 2, cylinder 14 has an interior chamber 16 into which is placed suspensions containing cells or membrane vesicles to be fused. Interior chamber 16 is beveled at its lower end and terminates in a central, axially extending bore defining pellet chamber 18. The beveling of interior chamber 16 facilitates channeling of cells or membrane vesicles during centrifugation into pellet chamber 18. As shown in FIGS. 1, 2 & 9, pellet chamber 18 provides a holding means for a plurality of tiers of components, and thereby provides a means by which defined and alternating tiers can be formed. In addition to providing a holding means for a plurality of tiers of components, an additional factor to limit the range of dimensions of pellet chamber 18 is the size (diameter) of cells or membrane vesicles to be fused. In that regard, for proper formation of a plurality of tiers, the height of pellet chamber 18 may be greater than 1 mm. For purposes of illustration only, and not limitation, the diameter of pellet chamber 18 may range from about 1 to about 5 mm.

Figure 3:
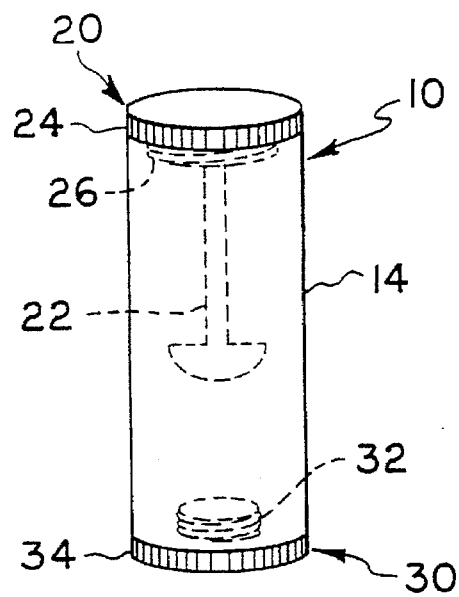
FIG. 3 is a perspective view of the apparatus for electrofusion.
Figure 4:
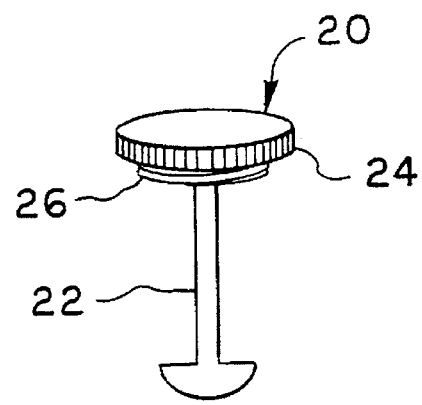
FIG. 4 is a perspective view of a first embodiment of a cap with top electrode for the apparatus for electrofusion.

In this first embodiment, the apparatus 10 according to the present invention further comprises a cap 20 which supports a first electrode or top electrode 22 within interior chamber 16, and also seals the upper end of interior chamber 16. As shown in FIGS. 3, 4 & 6, in this first embodiment, the cap 20 has a base disk portion 24 which preferably is grooved or ribbed to provide gripping means by which a user may manipulate cap 20. Cap 20 further comprises a cylindrical body portion 26 which snugly fits into and seals the upper end of interior chamber 16. In a preferred embodiment, body portion 26 is a threaded shaft, and the upper end of interior chamber 16 is threaded. Thus to seal apparatus 10, a user may grip cap 20 by base disk portion 24, and rotate cap 20 such that and until body portion 26 is threadingly engaged and tightly received by the upper end of interior chamber 16. However, it will be apparent to one skilled in the art that a snug fit and seal between body portion 26 and upper end of interior chamber 16 can be attained with means known in the art other than by threaded engagement. Base disk portion 24, body portion 26, and top electrode 22 of cap 20 are preferably formed of stainless steel.

As shown in FIGS. 1 & 3, top electrode 22 extends downwardly from cap 20 to conductively communicate with and be submerged in pulse medium contained within interior chamber 16 in the electrofusion process. As shown in FIGS. 4 & 6, it is apparent that top electrode 22 can be manufactured in a variety of shapes, such as in a "plunger" form or as a straight elongate member, and effectively and efficiently serve its function as an electrode. In continuing this first embodiment, top electrode 22 is in a plunger form as illustrated in FIGS. 1, 3 & 4.

Apparatus 10 according to the present invention further comprises a bottom cap 30 which functions as a second electrode, bottom electrode 32. As shown in FIGS. 1–3 & 5, in this first embodiment the bottom cap 30 has a base disk portion 34 which preferably is grooved or ribbed to provide gripping means by which a user may manipulate bottom cap 30. Bottom cap 30 further comprises bottom electrode 32 which may be in the form of a cylindrical body portion that snugly fits into lower end of cylinder 14 and seals the lower end of pellet chamber 18. In a preferred embodiment, bottom electrode 32 is a threaded shaft, and the lower end of cylinder 14 is a threaded recess 42. Thus to seal apparatus 10 at its lower portion, a user may grip bottom cap 30 by base disk portion 34, and rotate bottom cap 30 such that and until bottom electrode 32 is threadingly engaged and tightly received by threaded recess 42 and the lower end of cylinder 14 such that the lower end of pellet chamber 18 is sealed. However, it will be apparent to one skilled in the art that such a snug fit and seal can be attained with means known in the art other than by threaded engagement. Base disk portion 34, and bottom electrode 32 of bottom cap 30 are preferably formed of stainless steel.

As shown in FIGS. 1, 2, & 9, bottom electrode 32 extends upwardly from bottom cap 30 to communicate with pellets formed in pellet chamber 18 in the electrofusion process. That is to say, by centrifuging components for electrofusion in apparatus 10 for forming a pellet of alternating tiers, such pellet is formed in pellet chamber 18, and on bottom electrode 32. Thus, one embodiment for electrofusion according to the method of the present invention involves an electrical circuit in apparatus 10 to be connected to a low pulse voltage generator, wherein the electrical circuit is formed by top cap 20 with top electrode 22 submerged in pulse medium contained within interior chamber 16; a pellet comprising a plurality of tiers with the uppermost tier in operative contact with the pulse medium, with the pellet being formed on bottom electrode 32; and bottom electrode 32.

EXAMPLE 2

In this Example is illustrated electrofusion using the method according to the present invention, wherein the electrofusion is between at least two different types of cells. Further, electrofusion was performed to create proliferating hybrid cells comprising fused cells formed of the two different cell types. To illustrate this embodiment, cells from mouse myeloma cell line SP2/0, and lymphocytes from naive BALB/c mice were electrofused to form hybridomas (a hybrid SP2-lymphocyte cell). It is important to note that SP2 cells differ in size when compared to that of the BALB/c lymphocytes.

Prior to electrofusion the cells were prepared as follows. SP2 myeloma cells were cultured at 37° C. with 5% $CO_2$ in culture medium containing 20 µg/ml 8-azaguinine, 1.5 g/l $NaHCO_3$, 10% fetal bovine serum (FBS) and 0.6% of an antibiotic mixture. The cells were grown to exponential growth, and only cell cultures with a $\geq 95\%$ viability as determined by trypan blue exclusion test, were selected for electrofusion. The cells were harvested by centrifugation, washed with culture medium, and cell concentration was determined by using a hemacytometer. BALB/c lymphocytes were isolated from the spleens of BALB/c naive mice, resuspended and washed in culture medium containing 10% FBS, and counted to determine cell concentration. In preparing for electrofusion, both SP2 cells and the BALB/c lymphocytes were kept at room temperature to improve the efficiency of obtaining hybrid clones.

As illustrated in FIG. 9, a 5 tier cell pellet was formed by alternating tiers of lymphocytes and SP2 cells. Use of apparatus 10 is described herein as an illustration of how the cell pellet was formed. However, it will be apparent to those skilled in the art that means having a pellet chamber other than apparatus 10 can be used to practice the method of the invention. Medium containing $5 \times 10^5$ lymphocytes was placed into apparatus 10 of the present invention. Apparatus 10 was placed into a centrifuge tube held in a standard table top centrifuge. Centrifugation was performed for 10 seconds at 2200 X g. The supernatant above pellet chamber 18 was carefully removed so as not to disturb the cell pellet thus formed. Medium containing $2 \times 10^4$ SP2 cells was carefully placed into apparatus 10, centrifugation was performed for 10 seconds at 2200 X g, and the supernatant above pellet chamber 18 was carefully removed. This procedure was repeated by adding alternating tiers of lymphocytes ($5 \times 10^5$ cells/tier) and SP2 cells ($2 \times 10^4$ cells/tier). After the 5 tier cell pellet was formed, 0.5 ml of a pulse medium (125 mM KCl, 15 mM NaCl, 1.2 mM $MgCl_2$, 25 mM Hepes, 3 mM glucose, pH 7.4, with 20% FBS) was added.

Figure 10:
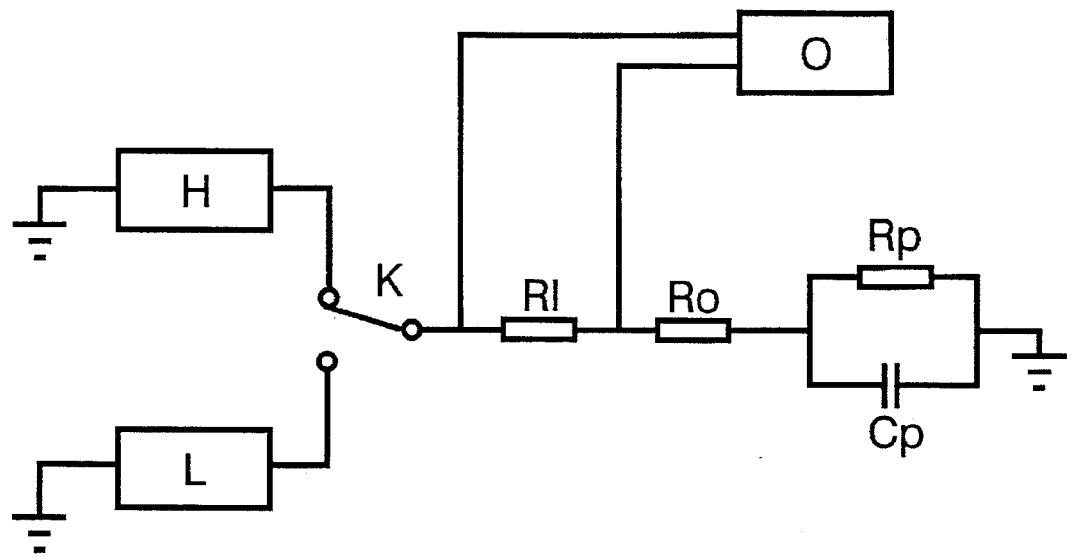
FIG. 10 is a simplified electrical circuit diagram employed in an embodiment of electrofusion according to the method of the present invention, wherein H: high voltage pulse generator; L: low voltage function generator; O: oscilloscope; $R_L$: Loading resistance; $R_p$: pellet resistance; $C_p$: pellet capacitance; and k: switch.

Although apparatus 10 (or other suitable container) containing the 5 tier cell pellet can be removed from the centrifuge to apply a voltage by a voltage pulse generator, in the present illustration the centrifuge was setup so that electrofusion could take place while apparatus 10 was inside the centrifuge. This setup involved two coaxial brass contact discs, separated by a spacer-insulator, which were fixed on the axle of the rotor. A pair of carbon brushes was fixed onto the centrifuge cover to provide electrical connections between apparatus 10 contained within the centrifuge, and voltage pulse generator contained outside of the centrifuge. Thus, the voltage pulses inducing electrofusion can be applied to the cell pellet either during centrifugation or with apparatus 10 in a stationary position. FIG. 10 illustrates an equivalent electrical circuit for applying pulses and for measuring resistance of a pellet.

After the 5 tier cell pellet was formed, the sample containing the pulse medium was subjected to an additional 1 minute of centrifugation. The cell pellet was subjected to multiple pulses within 30 second intervals using a voltage pulse generator. While a single pulse may be sufficient to promote cell fusion, multiple pulses appear advantageous over a single pulse as it was observed that preceding pulse-induced colloidal osmotic swelling of the cells promoted better membrane contact for fusion. To illustrate the dependency of fusion (hybridoma forming) efficiency on field strength (voltage), various voltages in the range of 0 volts to 400 volts were tested. In this illustration of the method according to the present invention, 3 pulses were used. The pulsed cells were then incubated at 37° C. for 20 minutes. This post-pulse incubation is important for the recovery and resealing of electropores of fused cells. Following the post-pulse incubation, the fused cells were resuspended in post-pulse cell culture medium (0.5% HAT medium) and placed in wells of a tissue culture plate. The wells also contained mouse peripheral macrophage feeder layer cells. While other media may be used to culture the pulsed cells, 0.5% HAT medium was found to be a suitable post-pulse cell culture medium for fused cell recovery. After cell culture for 24 hours in the post-pulse cell culture medium, 100% HAT medium (10 mM hypoxanthine, 40 mM aminoptern, 1.6 mM thymidine in minimal essential medium containing 10% FBS, 20 µg 8-azaguinine, 0.6% antibiotic mixture) was added to select for the growth of hybridoma cells. On day 7 of culture, fresh 100% HAT medium was added again. Seven to fourteen days post-pulse, the number of clones in culture were counted, wherein a clone containing more than 10 healthy cells was considered to be a clone formed from a proliferating hybridoma. The count of hybridomas was confirmed after vigorous growth of clones in HAT medium after 10 to 20 days.

Figure 11:
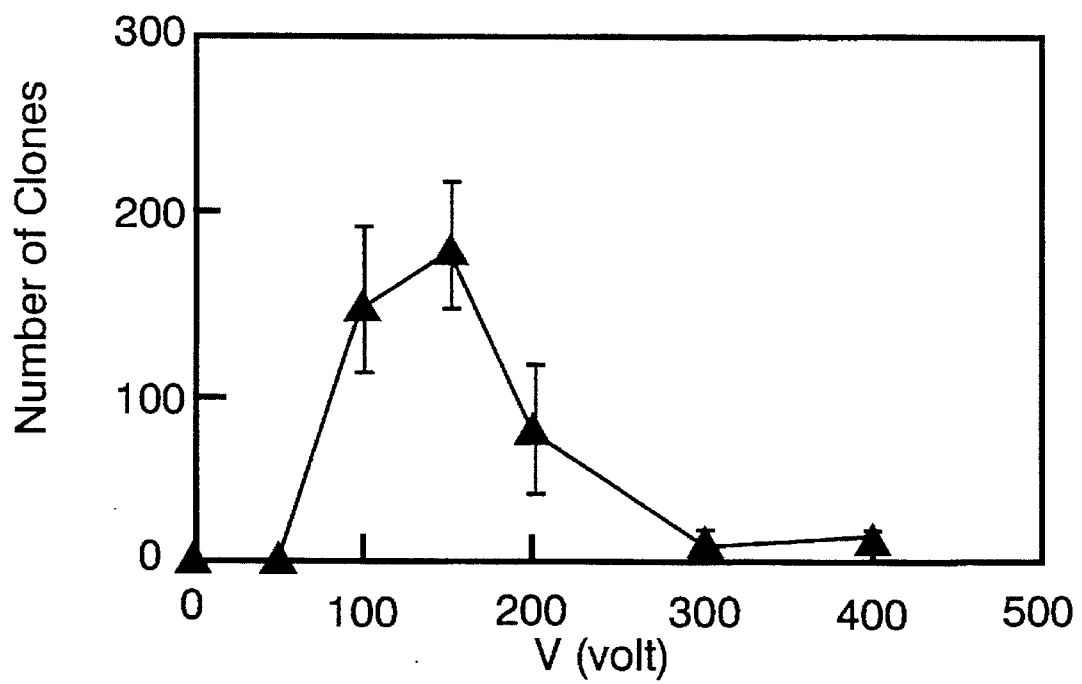
FIG. 11 is a graph illustrating the effect of pulse strength on the yield of hybrid clones between SP2 cells and lymphocytes.

As shown in FIG. 11, the yield of hybrid clones (clones formed from hybridomas) and the efficiency of hybridoma formation is dependent on the field strength of the pulse. Using the conditions described in this illustration, a field strength ranging from about 100 to about 150 volts gave the optimum hybridoma formation efficiency. This optimum and unexpected efficiency was estimated to be one out of every 200–400 SP2 cells (0.25% to 0.5%) fused with lymphocyte (s) in forming a hybridoma that survived post-pulse selection. However, and under the conditions described in this illustration, when the field strength was too low (<50 volts) or too high (>200 volts), the number of hybrid clones decreases significantly. As shown in FIG. 11, the control (i.e. no pulse or 0 voltage) resulted in no hybrid clones.

It is important to note that there is a significant distinction between fusion percentage and efficiency of hybridoma formation. To evaluate the fusion percentage, lymphocytes were first labeled with a membrane dye by contacting the lymphocytes with a solution containing a fluorescent dye (e.g., rhodamine-phosphatidyl ethanolamine, or 1,1' dioctadecyl-3,3,3',3'tetramethylindocarbocyanine or "DiI"). The lymphocytes were then washed and fused with SP2 cells according to the method of the present invention using multiple pulses of 150 volts. By a membrane dye mixing assay, it was observed that 60 to 70% of the SP2 cells were fused with the prelabeled lymphocytes. Thus, hybridoma formation and survival involves factors other than fusion alone. The membrane dye mixing assay was calculated as:

$$(N_{labelled}/N_{total}) \times 100\%$$

wherein $N_{labelled}$ is the number of target cells with fluorescence obtained from membrane dye mixing, and $N_{total}$ is the total number of target cells.

While this embodiment was illustrated with SP2 cells and lymphocytes, it will be apparent to one skilled in the art from the preceding and foregoing description that variations can be made in practicing the method according to the present invention. For example, cells of heterogenous size, other than SP2 cells and lymphocytes, may be fused. The speed of centrifugation will vary depending on the resiliency to centrifugal forces exhibited by the membranes of the cells desired to be fused. Depending on the cell type, typically centrifugation will fall within the range of about 500 X g to about 2500 X g.

It will be apparent to one skilled in the art that the efficiency of hybridoma formation from desired cells can be enhanced by optimizing pulse and cell parameters (number of pulses, pulse field strength, number of cells per tier, number of tiers), pulse medium effects, and post-pulse recovery. What distinguishes the method according to the present invention from other electrofusion systems is the use of a plurality of alternating tiers in a cell pellet, and the use of multiple low voltage pulses (typically less than 500 volts). It is known that the pulse mediums typically used for electroporation or electrofusion may vary in tonicity, ionic strength, and content. While these variations will likely affect the resistance of the pellet, it has been found that either high conductivity or low conductivity buffered solutions may be used in the method according to the present invention. It is also known in the art that post-pulse recovery medium for membrane resealing and cell recovery may vary in composition. However, for efficient cell recovery, the compositions of such media appears to require divalent cations such as calcium and/or magnesium ions.

EXAMPLE 3

This Example is a second embodiment illustrating electrofusion using the method according to the present invention, wherein the electrofusion is between at least two different types of cells. To illustrate this embodiment, cells from cell line CHO (Chinese hamster ovary; 15 μm in diameter) and comparatively smaller human erythrocytes (6 μm in diameter) were electrofused according to the method of the present invention.

Prior to electrofusion, the cells were prepared as follows. CHO cells were cultured at 37° C. with 5% $CO_2$ in culture medium (F10 medium) containing 15% FBS and 1% of an antibiotic mixture. The cells were grown to exponential growth, and only cell cultures with a ≧95% viability as determined by a trypan blue exclusion test, were selected for electrofusion. The cells were harvested by trypsinization, centrifugation, washed with culture medium, and then cell concentration was determined by using a hemacytometer. Human erythrocytes were isolated from the blood of healthy donors. The erythrocytes were washed in a sodium rich physiologic salt solution (150 mM NaCl, 3 mM KCl, 5 mM NaPi, pH 7.4) at 700 X g to remove plasma proteins, platelets and white cells. For some experiments, the washed erythrocytes were labeled with a fluorescent membrane dye (e.g. DiI). In preparing for electrofusion, both types of cells were kept at room temperature to improve the efficiency of fusion.

Using the methods and means as described in detail in Examples 1 and 2, a 5 tier cell pellet was formed by alternating tiers of erythrocytes and CHO cells. Briefly, a volume of solution containing approximately $1.5 \times 10^6$ erythrocytes was pelleted for 20 seconds at 700 X g to form a tier of cells. The supernatant above the pellet chamber was carefully removed so as not to disturb the cell tier thus formed. Medium containing approximately $3 \times 10^4$ to $4 \times 10^4$ CHO cells was carefully placed over the pellet chamber, centrifugation was performed for 20 seconds at 700 X g, and the supernatant above the pellet chamber was carefully removed. This procedure was repeated by adding alternating tiers of erythrocytes ($1.5 \times 10^6$ cells/tier) and CHO cells ($3 \times 10^4$ to $4 \times 10^4$ cells/tier). After the 5 tier cell pellet was formed, 0.5 ml of a pulse medium (PBS) was added, and the sample was then subjected to an additional 1 minute of centrifugation.

Figure 12:
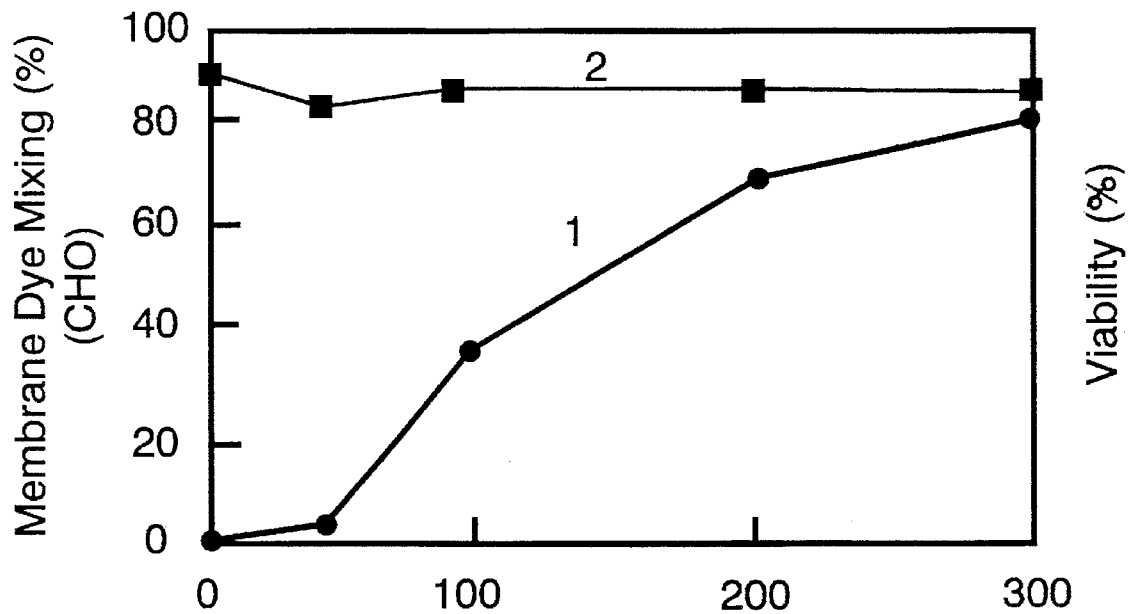
FIG. 12 is a graph illustrating the effect of pulse strength on the viability and fusion efficiency of CHO cells with erythrocytes.

The cell pellet was subjected to multiple pulses at 60 second intervals using a voltage pulse generator. To illustrate the dependency of fusion efficiency on field strength, various voltages in the range of 0 volts to 300 volts were tested. In this illustration of the method according to the present invention, 4 pulses (80 μs) were used. The pulsed cells were then centrifuged at 700 X g for an additional 5 minutes. The cells were then resuspended in a post-pulse cell culture medium and analyzed for fluorescence either immediately or after incubation at 37° C. As shown in FIG. 12, the viability of CHO cells (■) and the fusion efficiency between CHO cells and erythrocytes (●) were compared for dependency on the field strength of the pulse. Viability was assessed by using a trypan blue exclusion test, whereas fusion efficiency was evaluated by fluorescence in a membrane dye mixing assay. Using the conditions described in this illustration, a field strength of 300 volts resulted in optimum and unexpected fusion efficiency reaching ≧80%, whereas viability of CHO cells remained relatively constant at about 90% over the range of field strengths tested. As shown in FIG. 12, the control (i.e. no pulse or 0 voltage) resulted in no observed fusion.

EXAMPLE 4

This Example is a third embodiment illustrating electrofusion using the method according to the present invention, wherein the electrofusion is between at least two different types of cells. However, this third embodiment is used to illustrate the content mixing features which can be accomplished using the method according to the present invention. The content mixing experiments were performed to:

(a) confirm that the membrane dye mixing assay using the fluorescent dye was specifically due to cell fusion, and not an artifact of the very close membrane contact created by the pulse-induced colloidal osmotic swelling; and (b) demonstrate that membrane vesicles may be loaded with exogenous macromolecules, and then fused to desired target cells in a process of delivering exogenous macromolecules into target cells ex vivo for therapeutic or prophylactic applications (e.g., mediating drug or gene transfer into target cells).

To illustrate this embodiment, cells from either cell line L1210 (leukemic cells) or CHO were electrofused with comparatively smaller human erythrocyte ghost cells using the method according to the present invention. Prior to electrofusion, the cells were prepared as follows. CHO cells were prepared as described previously. L1210 cells were cultured at 37° C. with 5% $CO_2$ in culture medium (RPMI-1640 medium) containing 10% of a serum-like supplement and 0.1 mg/ml of gentamicin. The cells were grown to exponential growth, and only cell cultures with a ≧95% viability as determined by a trypan blue exclusion test, were selected for electrofusion. The cells were harvested by centrifugation, washed with culture medium, and then cell concentration was determined by using a hemacytometer.

Human erythrocytes were isolated from the blood of healthy donors as described previously. Erythrocyte ghosts (representative of membrane vesicles) were formed and loaded with fluorescein isothiocyanate dextran (FITC-dextran, representative of exogenous macromolecules) according to a previously reported method (Yoshihiro, 1993, *Methods in Enzymology*, Vol. 221:306–317). Briefly, potassium rich physiologic salt solution ("rPBS", 3 mM NaCl, 150 mM KCl, 5 mM NaPi, pH 7.4) was used to wash erythrocytes. A 0.1 ml volume of rPBS containing $10^{10}$/ml erythrocytes, and three volumes of FITC-dextran medium (10 mg/ml in rPBS, 42 Kd molecular mass, in 0.3 ml) were placed in a dialysis bag (molecular size cutoff of 12000–14000 Kd), and then immersed in a 500 ml of diluted rPBS (⅙ rPBS) for 0.5 hours at 4° C. Another incubation for 0.5 hours in 500 ml PBS at 25° C. was performed to reseal the osmotic pores on the ghost membranes. The loaded and resealed ghost cells were washed several times in PBS, and in a balanced salt solution. The washed ghost cells were kept at 4° C. before use, and could be stored for up to three days without significant leakage or change of loading efficiency. For some experiments, the ghost cells were also labeled with a membrane dye (DiI). In preparing for electrofusion, both types of cells were kept at room temperature to improve the efficiency of fusion.

Using the methods and means as described in detail in Examples 1–3, a 5 tier cell pellet was formed by alternating tiers of ghost cells and L1210 cells. Briefly, a volume of solution containing approximately $1.5 \times 10^6$ ghost cells was pelleted for 20 seconds at 700 X g to form a tier of cells. The supernatant above the pellet chamber was carefully removed so as not to disturb the vesicle tier thus formed. Medium containing approximately $6\times10^4$ to $8\times10^4$ L1210 cells was carefully placed over the pellet chamber, centrifugation was performed for 20 seconds at 700 X g, and the supernatant above the pellet chamber was carefully removed. This procedure was repeated by adding alternating tiers of ghost cells ($1.5\times10^6$ cells/tier) and L1210 cells ($6\times10^4$ to $8\times10^4$ cells/tier). After the 5 tier cell-vesicle pellet was formed, 0.5 ml of a pulse medium (rPBS) was added, and the sample was then subjected to an additional 1 minute of centrifugation. Cell-vesicle pellets made of CHO and ghost cells was prepared in a similar fashion except that CHO cells were used at $3\times10^4$ to $4\times10^4$ cells/tier.

The cell-vesicle pellet was subjected to multiple pulses at 60 second intervals using a voltage pulse generator. To illustrate the dependency of fusion efficiency on field strength, various voltages in the range of 0 volts to 500 volts were tested. In this illustration of the method according to the present invention, 4 pulses (80 μs) were used. The pulsed cells and vesicles were then centrifuged at 700 X g for an additional 5 minutes. The cells-vesicles were then resuspended in a post-pulse cell culture medium and analyzed for fluorescence either immediately or after incubation at 37° C. Fusion efficiency was evaluated by fluorescence in a content mixing assay. The content mixing assay was calculated as:

$$(N_{labelled}/N_{total})\times 100\%$$

wherein $N_{labelled}$ is the number of target cells with fluorescence obtained from content mixing, and $N_{total}$ is the total number of target cells.

Figure 13:
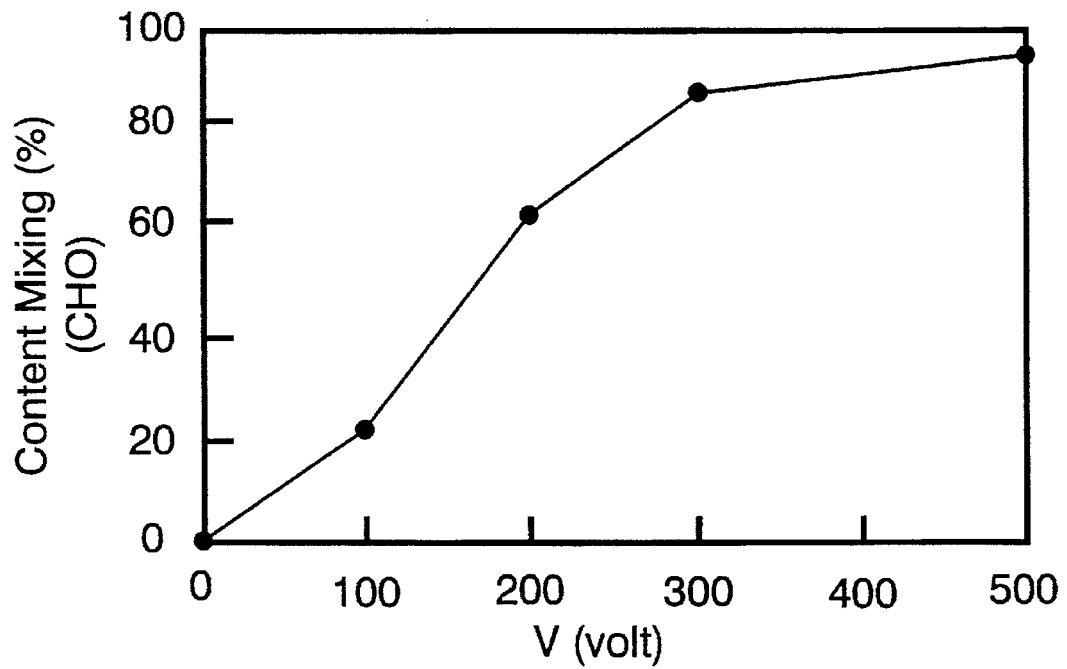
FIG. 13 is a graph illustrating the effect of pulse strength on the fusion efficiency of CHO cells with erythrocyte ghost cells.
Figure 14:
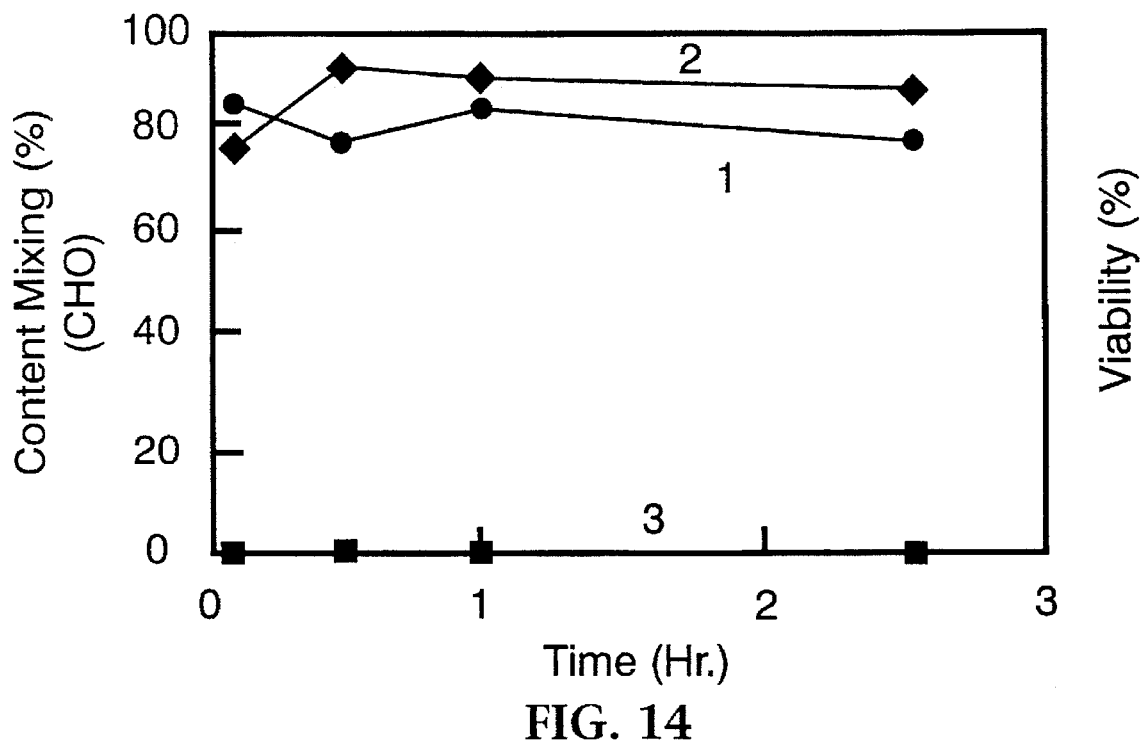
FIG. 14 is a graph illustrating the effect of post-pulse incubation on the viability and loading efficiency of CHO cells.

As shown in FIG. 13, the fusion efficiency between CHO cells and ghost cells was dependent on the field strength of the pulse. The trend of fusion efficiency (demonstrated by content mixing; ●) vs. field strength in FIG. 13, parallels the trend of fusion vs. field strength demonstrated by membrane dye mixing in FIG. 12. The fused cells were monitored over time, as shown in FIG. 14. As shown in FIG. 14, a field strength of 300 volts or 500 volts resulted in optimum and unexpected fusion efficiency reaching $\geq 80\%$, while maintaining a viability (♦) $\geq 80\%$. The control (i.e. no pulse or 0 voltage; ■) resulted in no observed fusion. In order to further demonstrate that content mixing occurred during fusion between CHO and ghost cells, ghost cells were doubly labelled; i.e., by membrane dye (DiI) and by loading FITC-dextran. Using the methods outlined in Examples 1–4, fusion was performed between the CHO cells and doubly labelled ghosts. The fusion efficiency as measured by membrane dye mixing and as measured by content mixing, and as compared to viability, is shown in Table 1. These results show that fusion efficiency as measured by membrane dye mixing is consistently higher than that by content mixing, but both efficiencies are as high as 80–90%. The controls showed neither membrane dye mixing nor content mixing. While membrane dye mixing was consistently higher than content mixing, it was noted during counting that there appeared to be no CHO cell with content mixing but without membrane dye mixing. Both assays, content mixing and membrane dye mixing, support the occurrence of high efficiency fusion in the method according to the present invention. Further, the results demonstrate that membrane vesicles may be loaded with exogenous macromolecules, and then fused to desired target cells in a process of delivering exogenous macromolecules into target cells with high efficiency.

TABLE 1

|  | content mixing | membrane dye mixing | viability |
| --- | --- | --- | --- |
| pulsed cells | 82% | 90% | 83% |
| control cells | 0% | 0% | 95% |

Figure 15:
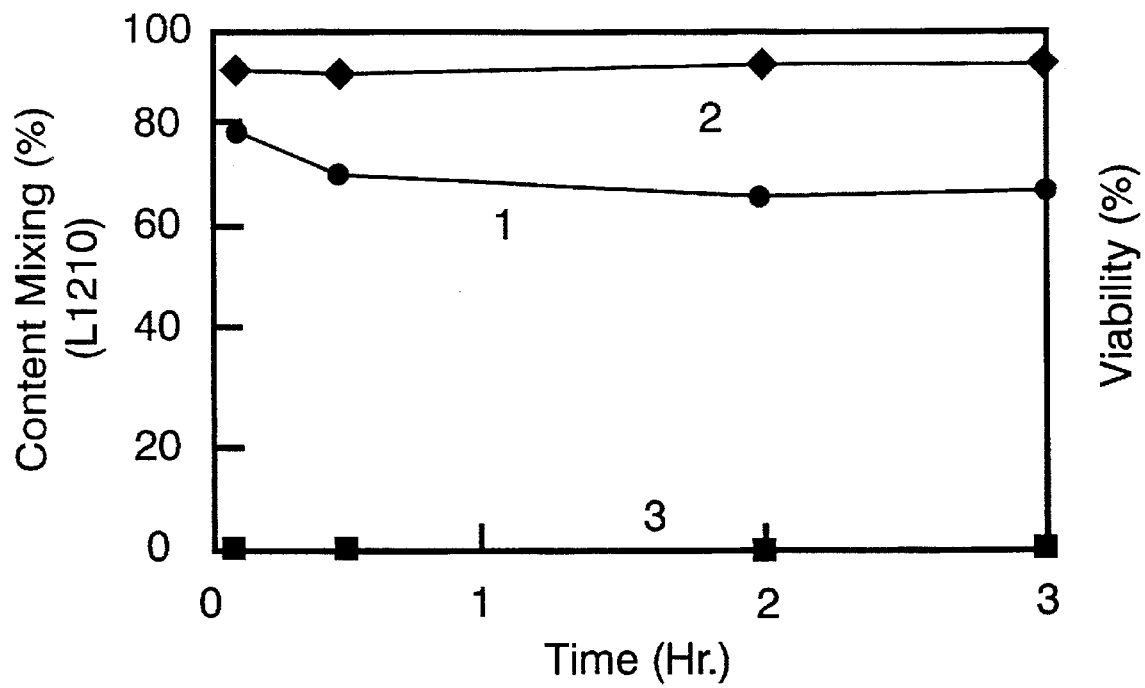
FIG. 15 is a graph illustrating the effect of post-pulse incubation on the viability and loading efficiency of L1210 cells.

The fusion efficiency between L1210 and ghost cells, as measured by content mixing (●), was compared to viability (♦) after four 300 volt (80 μs) and followed over a 3 hour post-pulse incubation period is shown in FIG. 15. The results show that over the 3 hour period, content mixing and viability of the L1210 cells remained approximately 70% and 90%, respectively. The control (i.e. no pulse or 0 voltage; ■) resulted in no observed fusion. Using the methods as described in Examples 1–4, L1210 and ghost cells in a cell-vesicle pellet were pulsed (4 pulses) with higher field strength at 400 V (80 μs) in an attempt to increase fusion efficiency as measured by content mixing. The results showed that although initial content mixing and viability were as high as 90%, they decreased to levels of 36% and 52%, respectively, after a 30 minute post-pulse incubation.

Fusion between L1210 and doubly labelled ghost cells was performed using the methods outlined in Examples 1–4. The fusion efficiency as measured by membrane dye mixing and as measured by content mixing, and as compared to viability, is shown in Table 2. These results show that fusion efficiency as measured by membrane dye mixing was 100%, whereas that as measured by content mixing was 76%. The controls showed neither membrane dye mixing nor content mixing.

TABLE 2

|  | content mixing | membrane dye mixing | viability |
| --- | --- | --- | --- |
| pulsed cells | 76% | 100% | 82% |
| control cells | 0% | 0% | 95% |

EXAMPLE 5

This Example illustrates a utility inherent in the embodiments illustrated in Examples 3 and 4 for electrofusion using the method according to the present invention. Electro-insertion is a technique that has been previously described, wherein an exogenous molecule (e.g., a cell receptor) is implanted into a target cell's membrane. This technique involves adding the exogenous molecule to a suspension of target cells, and the mixture is electroporate. The technique has resulted in the expression of the exogenous molecule in such a way as to maintain biological activity of the molecule inserted into the cell membrane of the target cells. CD4 molecules were inserted into the membranes of red blood cells such that the inserted CD4 maintained reactivity with various anti-CD4 antibodies (Mouneimne et al., 1990, *Biochimica et Biophysica Acta*, 1027:53–58). Also, human glycophorin has been inserted into mouse erythrocytes (Mouneimne et al., 1991, *Biochimica et Biophysica Acta*, 1066:83–89). However, it appears that not all proteins may be inserted with the technique (Mouneimne et al., 1990, supra).

Insertion of endogenous and/or exogenous macromolecules into the membranes of target cells has therapeutic uses including, but not limited to, immune modulation and vaccines (see, e.g., Harokopakis et al., 1995, *J. Immunol. Methods*, 185:31–42; Ifversen et al., 1995, *Immunology*, 84:111–116; and Glenn et al., 1995, *Immunol. Lett.*, 47:73–78). Illustrated in Example 3 is an embodiment for electrofusion using the method according to the present invention, wherein fused in a cell pellet are at least two different cell types. According to the method of the present invention, and as evidenced by membrane dye mixing shown in FIG. 12 for fusion between CHO cells and erythrocytes, macromolecules endogenous to one type of cell and present in that cell's membrane are incorporated into the membrane of the target cell of a different cell type upon fusion between the membranes. For example, fusion between CHO cells (target cells) and erythrocytes results in a hybrid cell containing a cell membrane comprised of CHO cell surface receptors, proteins, glycoproteins, and the like, and erythrocyte cell surface receptors, proteins, glycoproteins, and the like. Since CHO cells are larger in size than erythrocytes, when a CHO cell and erythrocyte fuse using the method of the present invention, the hybrid cell will have a cell membrane comprised mostly of CHO membrane components. Added to that are, for example, endogenous macromolecules such as erythrocyte ABO blood group antigens. Thus, endogenous macromolecules may be inserted into the membranes target cells with high efficiency and high viability using the method of electrofusion according to the present invention.

Illustrated in Example 4 is an embodiment for electrofusion using the method according to the present invention, wherein fused in a cell-vesicle pellet are a target cell type and a membrane vesicle. According to the method of the present invention, and as evidenced by membrane dye mixing shown in Tables 1 and 2, a cell type and membrane vesicle may be fused with high efficiency and high viability. One or more type of exogenous macromolecules may be inserted or incorporated into the membrane vesicle using any one of several techniques known in the art (see, e.g. Golstein et al., 1995, *Biochem. J.*, 312:543–548; Harokopakis et al., 1995, supra; Ifversen et al., 1995, supra; and Glenn et al., 1995, supra). The exogenous macromolecules inserted in the membrane of the membrane vesicle becomes incorporated into the membrane of the target cell upon fusion between the membrane vesicle and the membrane of the target cell. Thus, exogenous macromolecules may be inserted into the membranes target cells with high efficiency and high viability using the method of electrofusion according to the present invention. Further, the method according to the present invention may be used to incorporate a combination of at least one exogenous macromolecule and at least one endogenous macromolecule into the target cell membrane.

EXAMPLE 6

This Example illustrates considerations for and modifications of electrofusion using the method according to the present invention. Using a modification of the methods outlined in Examples 1–4, fusion was performed between the CHO cells and ghosts cells. In Example 3 and Example 4, the ratio of the number of erythrocytes or ghost cells to that of CHO cells is approximately 50. A modification was performed to decrease this ratio by reducing the number of ghost cells per tier, but increasing the number of tiers from 5 to 11 (while maintaining approximately the same total number of cells used in preparing the pellet). Thus, in forming the cell-vesicle pellet, 11 tiers were formed by reducing the number of ghosts cells per tier but maintaining approximately the same pellet resistance. The fusion efficiency as measured by membrane dye mixing and as measured by content mixing, and as compared to viability. The results showed that high efficiency and high viability were observed which were comparable to that shown in Examples 3 and 4. Thus, a number of tiers greater than 5 can be used in the method according to the present invention. However, in another modification, the cell-vesicle pellet was formed of 5 tiers of ghost cells and CHO cells as described according to Examples 3 and 4 except that the number of CHO was significantly increased per tier of CHO cells. It was noted that fusion using this modification resulted in undesirable fusion among CHO cells themselves. Thus, if high efficiency fusion is desired between two different cell types, or a cell type and a membrane vesicle, there is a functional limitation as to the number of cells or vesicles per tier when forming a pellet.

One skilled in the art would appreciate that depending on the cell types to be fused, or the cell type to be fused with the membrane vesicle, the voltage pulse used in the method of electrofusion according to the present invention may vary. In that regard, depending on the components to be electrofused, voltages in the range of 150 volts to 750 volts have been found to achieve the high efficiency and high viability in the method of electrofusion according to the present invention.

To evaluate the observed benefit of multiple pulses, the post pulse pellet resistance was measured during a process of electrofusion of CHO cells with erythrocytes or ghost cells at 300 volts using 4 pulses according to the method of the present invention. During the pulses, the pellet resistance ($R_p$) dropped to zero, but seconds after pulses $R_p$ rose even higher than the previous rise (up to approximately 280 ohms) until the fourth pulse. After the fourth pulse, $R_p$ did not recover completely. These results indicate that after each of the first three pulses, $R_p$ rose to a level higher than the previous rise due to tighter membrane contact as a result of pulse-induced colloidal osmotic swelling of cells in the pellet. However, the observance that after the fourth pulse $R_p$ reduced from the level attained after the third pulse is an indication that irreversible membrane breakdown begins to occur. Thus, from these $R_p$ measurements, and using the method according to the present invention, a number of pulses greater than 4 may not be desirable for high fusion efficiency and high viability.

Since pellet resistance is in series with the loading resistance ($R_L$) and the resistance of the pulse medium contained in the electrofusion chamber ($R_o$; see FIG. 10), an increase in $R_p$ means a voltage distribution according to the formula of pulse voltage across the pellet ($V_p$):

$$V_p = (V \times R_p)/(R_L + R_o + R_p)$$

$V_p$ drops to a significantly low level within microseconds during the pulse. Once the cell membranes on a cell layer are broken down (usually a transmembrane potential of 0.5–1V), the voltage across the cells on that layer drops due to the decrease of $R_p$. In contrast, for cells pulsed and fused in suspension the transmembrane potential will decrease after membrane breakdown, but the same high voltage across cells is maintained during pulsing. Thus, the quick dropping of the voltage across the cells after membrane breakdown using the method according to the present invention allows the fused cells to suffer much less damage compared to cells pulsed and fused in suspension. Other advantages conferred by this quick dropping of voltage across the cells includes (a) the ability to use highly conductive pulse medium in the method according to the present invention; and (b) large target cells can be fused with smaller target cells or membrane vesicles and still maintain high viability.

It should be understood that while the invention has been described in detail herein, the examples were for illustrative purposes only. Other modifications of the embodiments of the present invention that are obvious to those of ordinary skill in the art of molecular and cellular biology, biophysics, and related disciplines are intended to be within the scope of the appended claims.

We claim:

1. An apparatus for electrofusing a pellet comprising a plurality of tiers, said apparatus comprising:
   a cylinder having an interior chamber into which is placed suspensions containing components selected from the group consisting of cells, membrane vesicles, and a combination thereof;
   a pellet chamber comprising an axially extending bore at the lower end of the interior chamber, wherein the pellet chamber provides a means for forming and holding a pellet comprising a plurality of tiers;
   a first cap means connected to an end of a first electrode and configured to removably fit and seal the upper end of the cylinder for positioning the first electrode to extend downwardly into the interior chamber; and
   a second cap means connected to a second electrode and configured to removably fit and seal the lower end of the cylinder for positioning the second electrode to extend to and contact the pellet chamber.

2. The apparatus according to claim 1, wherein the interior chamber is beveled to facilitate channeling of the components into the pellet chamber during centrifugation.

3. The apparatus according to claim 1, wherein the first and second cap means and the first and second electrodes are made of stainless steel.

4. An apparatus for electrofusing a pellet comprising a plurality of tiers, said apparatus comprising:
   a cylinder having an interior chamber;
   pulse medium contained within the interior chamber;
   a pellet chamber comprising an axially extending bore at the lower end of the interior chamber, wherein the pellet chamber provides a means for forming and holding a pellet comprising a plurality of tiers;
   a pellet in contact with the pulse medium and comprising a plurality of tiers of components to be fused, wherein the components are selected from the group consisting of cells of two different types, and cells and membrane vesicles.
   a first cap means connected to an end of a first electrode and configured to removably fit and seal the upper end of the cylinder for positioning the first electrode to extend downwardly into the interior chamber to conductively communicate with and be submerged in the pulse medium; and
   a second cap means connected to a second electrode and configured to removably fit and seal the lower end of the cylinder for positioning the second electrode to extend to and contact the pellet chamber, wherein the pellet is formed on a surface of the second electrode.

5. The apparatus according to claim 4, wherein the interior chamber is beveled to facilitate channeling of the components into pellet chamber during centrifugation.

6. The apparatus according to claim 4, wherein the first and second cap means and the first and second electrodes are made of stainless steel.

7. The apparatus according to claim 4, wherein the components are cells of two different types, and wherein the cell types are heterogenous in size compared to the other cell type.

8. The apparatus according to claim 4, wherein the components are cells and membrane vesicles, wherein the membrane vesicles have inserted into their membranes at least one type of macromolecule selected from the group consisting of an exogenous macromolecule, an endogenous macromolecule, and a combination thereof.

9. The apparatus according to claim 4, wherein the components are cells and membrane vesicles, wherein the membrane vesicles are loaded with at least one exogenous macromolecules.

10. A method for delivering with high efficiency an exogenous macromolecule into target cells by electrofusion, the method comprises:
    forming a cell-vesicle pellet comprised of a plurality of tiers, wherein the tiers comprise alternating layers of target cells and membrane vesicles, and wherein the membrane vesicles are loaded with the exogenous macromolecule;
    contacting the cell-vesicle pellet with a pulse medium; and
    subjecting the pulse medium and cell-vesicle pellet to multiple pulses of voltage.

11. The method according to claim 10, wherein the voltage is delivered by a means in which the pulse medium is in operative contact with a first electrode, and the cell-vesicle pellet is in operative contact with a second electrode.

12. The method according to claim 10, further comprising incubating the pulsed cells in a post-pulse culture medium.

13. The method according to claim 11, further comprising incubating the pulsed cells in a post-pulse culture medium.

14. The method according to claim 10, wherein the plurality of tiers comprise 5 tiers.

15. The method according to claim 14, wherein the 5 tiers are formed from a first tier comprising the loaded membrane vesicles, a second tier comprising the target cells, a third tier comprising the loaded membrane vesicles, a fourth tier comprising the target cells, and a fifth tier comprising the loaded membrane vesicles.

16. The method according to claim 10, wherein the multiple pulses comprise a number of pulses that range from 3 to 4, and wherein the voltage of said pulses is a voltage within the range of from 150 to 750 volts.

17. The method according to claim 16, further comprising incubating the pulsed cells in a post-pulse culture medium.

18. A method for electrofusing two different cell types in forming hybrid cells with high efficiency, the method comprises:
    forming a cell pellet comprised of a plurality of tiers, wherein the tiers comprise alternating layers of a first cell type and a second cell type;
    contacting the cell pellet with a pulse medium; and
    subjecting the pulse medium and cell pellet to multiple pulses of voltage.

19. The method according to claim 18, wherein the voltage is delivered by a means in which the pulse medium is in operative contact with a first electrode, and the cell pellet is in operative contact with a second electrode.

20. The method according to claim 18, further comprising incubating the pulsed cells in a post-pulse culture medium.

21. The method according to claim 19, further comprising incubating the pulsed cells in a post-pulse culture medium.

22. The method according to claim 18, wherein the cell types are heterogenous in size compared to the other cell type.

23. The method according to claim 18, wherein one cell type is a target cell and a macromolecule endogenous to the other cell type is inserted into the membrane of the target cell.

24. The method according to claim 18, wherein the plurality of tiers comprise 5 tiers.

25. The method according to claim 24, wherein the 5 tiers are formed from a first tier comprising the first cell type, a second tier comprising the second cell type, a third tier comprising the first cell type, a fourth tier comprising the second cell type, and a fifth tier comprising the first cell type.

26. The method according to claim 18, wherein the multiple pulses comprise a number of pulses that range from 3 to 4, and wherein the voltage of said pulses is a voltage within the range of from 150 to 750 volts.

27. The method according to claim 26, further comprising incubating the pulsed cells in a post-pulse culture medium.

28. A method for electrofusing two different cell types in forming hybrid cells with high efficiency and high viability, the method comprises:

forming a cell pellet comprised of a plurality of tiers, wherein the tiers comprise alternating layers of a first cell type and a second cell type;

contacting the cell pellet with a pulse medium; and subjecting the pulse medium and cell pellet to multiple pulses of voltage.

29. The method according to claim 28, wherein the voltage is delivered by a means in which the pulse medium is in operative contact with a first electrode, and the cell pellet is in operative contact with a second electrode.

30. The method according to claim 28, further comprising incubating the pulsed cells in a post-pulse culture medium.

31. The method according to claim 29, further comprising incubating the pulsed cells in a post-pulse culture medium.

32. The method according to claim 28, wherein the cell types are heterogenous in size compared to the other cell type.

33. The method according to claim 28, wherein the plurality of tiers comprise 5 tiers.

34. The method according to claim 33, wherein the 5 tiers are formed from a first tier comprising the first cell type, a second tier comprising the second cell type, a third tier comprising the first cell type, a fourth tier comprising the second cell type, and a fifth tier comprising the first cell type.

35. The method according to claim 28, wherein the multiple pulses comprise a number of pulses that range from 3 to 4, and wherein the voltage of said pulses is a voltage within the range of from 150 to 750 volts.

36. The method according to claim 35, further comprising incubating the pulsed cells in a post-pulse culture medium.

37. A method for delivering and inserting with high efficiency at least one type of exogenous macromolecules into a cell membrane of target cells by electrofusion, the method comprises:

forming a cell-vesicle pellet comprised of a plurality of tiers, wherein the tiers comprise alternating layers of target cells and membrane vesicles, and wherein the membrane vesicles contain the exogenous macromolecule inserted into their membrane;

contacting the cell-vesicle pellet with a pulse medium; and subjecting the pulse medium and cell-vesicle pellet to multiple pulses of voltage.

38. The method according to claim 37, wherein the voltage is delivered by a means in which the pulse medium is in operative contact with a first electrode, and the cell-vesicle pellet is in operative contact with a second electrode.

39. The method according to claim 37, further comprising incubating the pulsed cells in a post-pulse culture medium.

40. The method according to claim 38, further comprising incubating the pulsed cells in a post-pulse culture medium.

41. The method according to claim 37, wherein the plurality of tiers comprise 5 tiers.

42. The method according to claim 41, wherein the 5 tiers are formed from a first tier comprising the membrane vesicles, a second tier comprising the target cells, a third tier comprising the membrane vesicles, a fourth tier comprising the target cells, and a fifth tier comprising the membrane vesicles.

43. The method according to claim 37, wherein the multiple pulses comprise a number of pulses that range from 3 to 4, and wherein the voltage of said pulses is a voltage within the range of from 150 to 750 volts.

44. The method according to claim 43, further comprising incubating the pulsed cells in a post-pulse culture medium.

* * * * *